United States Patent [19]

Collins

[11] 4,002,074
[45] Jan. 11, 1977

[54] DEVICE AND METHOD FOR OBTAINING ONE OR MORE SAMPLES OF MOLLEN METAL

[76] Inventor: William J. Collins, 7005 Madison St., Merrillville, Ind. 46410

[22] Filed: May 26, 1976

[21] Appl. No.: 690,296

Related U.S. Application Data

[63] Continuation-in-part of Ser. No. 543,687, Jan. 24, 1975.

[52] U.S. Cl. .......................... 73/425.4 R; 73/DIG. 9
[51] Int. Cl.² .......................................... G01N 1/12
[58] Field of Search ............... 73/425.4 R, DIG. 9; 164/4

[56] References Cited

UNITED STATES PATENTS

| | | |
|---|---|---|
| 3,656,350 | 4/1972 | Collins .......................... 73/425.4 R |
| 3,693,449 | 9/1972 | Collins ................................. 73/354 |
| 3,751,986 | 8/1973 | Boron ........................... 73/425.4 R |
| 3,791,219 | 2/1974 | Falk .............................. 73/425.4 R |
| 3,798,974 | 3/1974 | Boron ........................... 73/425.4 R |
| 3,859,857 | 1/1975 | Falk .............................. 73/425.4 R |
| 3,905,238 | 9/1975 | Falk ................................. 73/425.6 |
| 3,915,014 | 10/1975 | Judge et al. ....................... 73/425.6 |

FOREIGN PATENTS OR APPLICATIONS 6,804,930  10/1968  Netherlands ................... 73/DIG. 9

Primary Examiner—S. Clement Swisher

[57] ABSTRACT

The invention involves providing a device or devices whereby one or more samples of liquid, such as molten metal, may be readily obtained from a mass or stream thereof.

26 Claims, 38 Drawing Figures

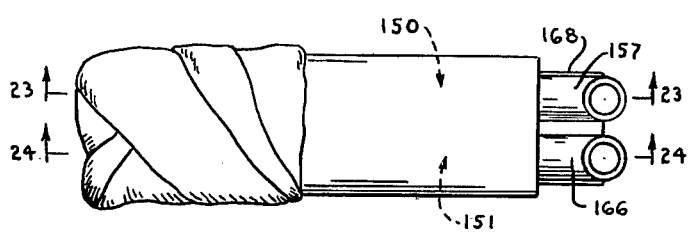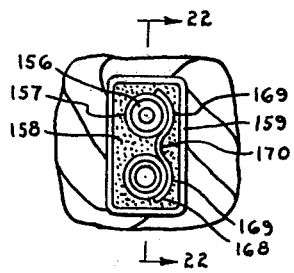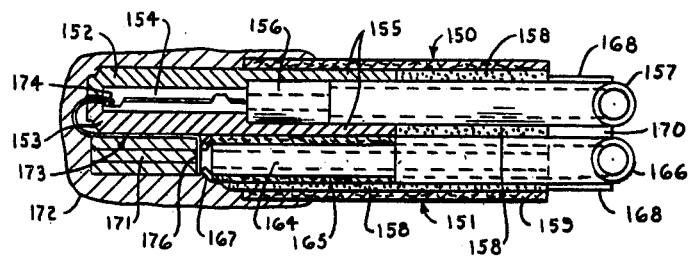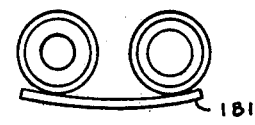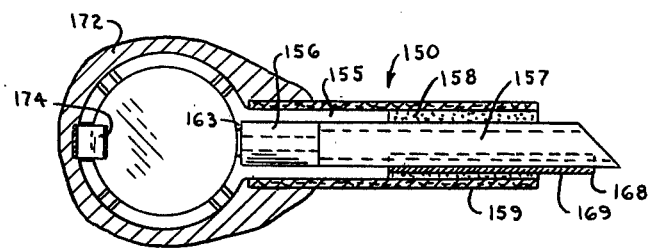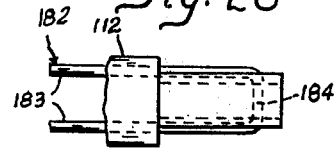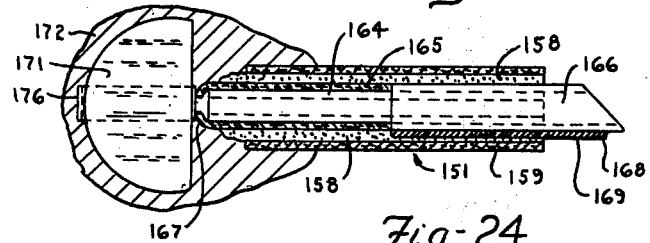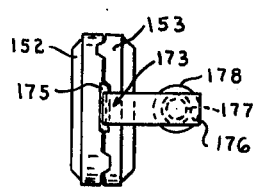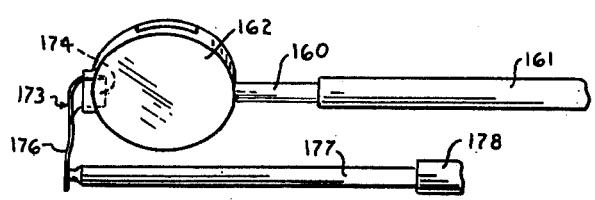

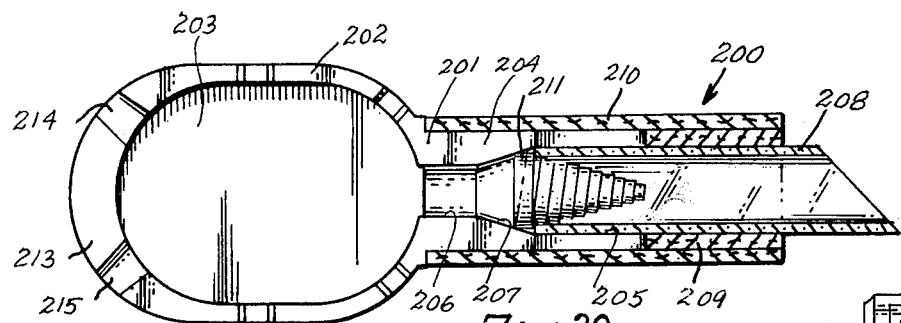
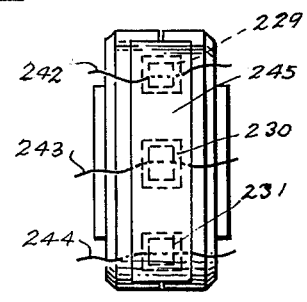
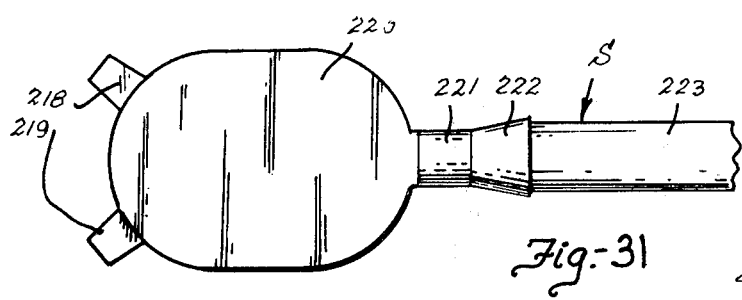
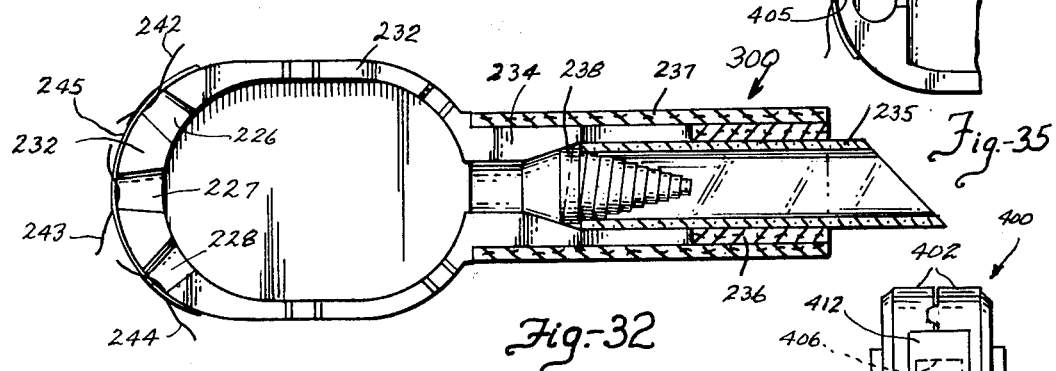
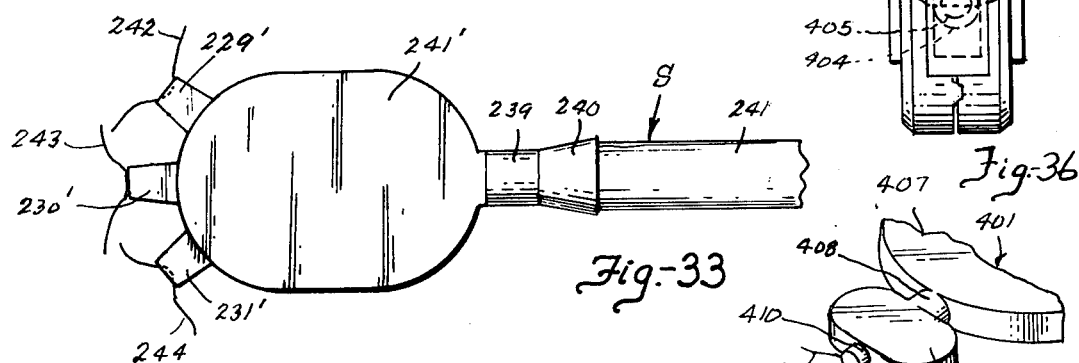

DEVICE AND METHOD FOR OBTAINING ONE OR MORE SAMPLES OF MOLLEN METAL

BACKGROUND OF INVENTION

This application is a continuation-in-part of my application Ser. No. 543,687 filed Jan. 24, 1975 and includes disclosures with respect to FIGS. 9 and 10 of my copending application Ser. No. 563,590 filed Mar. 31, 1975. Reference is also hereby made to may copending applications Ser. No. 563,581 filed Mar. 31, 1975; Ser. No. 595,155 filed July 11, 1975 and Ser. No, 656,660 filed Feb. 9, 1976 which disclosure devices comprising, among other things, a secondary chamber or chambers which are described and/or defined in various ways.

The invention relates to a device and method of extracting one or more samples of molten steel or other types of metal from a stream from the bottom of a ladle. A recognized fact is that the pouring of molten steels or other materials from the bottom of a ladle into the type of cavity or container which it will form; is momentarily exposed to the atmosphere causing a minute but indeterminable amount of contamination from the air. This effects the composition of the steel or other molten metals but is theorized to occur only at the skin or periphery of the molten stream. The stream in effect becomes a column extending from the bottom of a ladle to the top of the point where it begins to become a part of the casting. The teeming in the steel industry may form an ingot, or the metal may be caused to flow into another ladle, a tundish or some other receptacle. Evidence suggests that the techniques used in the steel industry may be applied to other metal industries. The recognition of this contamination makes it desirable to shorten this column length to the minimum giving it as little exposure to the atmosphere as possible. Because of this factor it is believed that the subject invention offers a setup whereby a sample can be more satisfactorily obtained than by other types of devices that have been utilized. It has been observed that by immersing other stream sampling devices directly into the molten column it is difficult to determine the intersection of the tip of the sampling device into the column, whereas crossing the stream laterally by employing a unique connector or holder carried by a lance, staff or wand, affords a clear view of the sampling device and its tangential penetration of the column of steel or other metal. The connector or holder and/or lance facilitates the opportunity of tilting the device at a sharper angle to the stream or molten metal column. Essentially the device can be laterally cross the molten metal column from either the right or left, cocking the sampling device to encourage the metal to momentarily penetrate an aperture or entrance provided in a tubular means constituting a component of the device. The cavity which receives the molten metal substantially freezes it to provide a sample or samples generally similar to those obtained by an immersion type of devices disclosed in my U.S. Pat. No. 3,552,214 dated Jan. 5, 1971.

A feature of my invention is the recognition that by supporting a glass tubular means leading into the mold with steel, cardboard or some other rigidizing reenforcing or supporting material I avoid the use of the traditional expensive quartz type tubing which many have felt was required to afford the necessary thermal and shock resistance known to emanate from the molten stream or molten column from the ladle, tundish or other source. By supporting a Pyrex glass tubular means with a suitable rigidizing material the shock resistance of the glass is buttressed for the infinitesimal second required to permit entrance of the required amount of metal to fill the vented cavity or receiving means provided for it. In previous patents that I have received directed to immersion molten metal samplers, the principle of a vented mold has been established as has the use of Pyrex glass tubing through which the metal flows into the mold cavity.

The presentation of the sampling device laterally cocked upwards at an angle presents a sufficient entrance or orifice to allow a flow of the metal into the receiving means. The venting provided in the device allows for immediate evacuation of residual air as well as providing the chill to freeze the molten sample. The holder or connector allows a presentation of the sampling device at any desired angle with reference to the longitudinal axis of the lance or staff as well as at any desired angle with reference to the flow of the stream or column of metal and may be considered to be a light weight clamp which if tubular can be mounted on a steel, aluminum or other light weight rigid column such as a staff, lance or wand as alluded to above. It is reasonably obvious that the presentation of a dark object such as the sampling device to the radiance emanating from the molten metal stream or column is more discernible when done laterally. The principle of presenting the sampling snout or entrance to the stream or column of molten metal is as simple as presenting it to a stream of water emanating from a faucet. The liquid must follow the path into which it is invited. A filling or sample is a simple matter of immersing the entrance or snout of the device far enough into the molten column or stream to avoid the possible contamination at the periphery of the molten column or stream as it is momentarily exposed to the atmosphere.

The minimal weight of the sampling device disclosed, coupled with a light weight presentation to the column or stream requires no additional paraphernalia to support its presentation to the stream or column. Grades of steel which must be deoxidized can be accommodated by providing adequate percentages of aluminum or other types of deoxidizing material which may be located where desired such as in the glass tubular means leading to the chamber of the device. The device may also be provided with an exit or venting tube or tubes of glass emanating snorkel-like from the chamber end opposite to that of the entrance.

With the foregoing in mind, an important object of the subject invention is to provide comprising wall structure forming what may be referred to as a chamber, receiving means, or cavity, tubular means communicating with an extending from said chamber and having an outer extremity provided with an entrance through which liquid may be caused to flow into said chamber, and means for supporting at least a portion of said outer extremity against possible damage when inserted into a supply of liquid, as well as afford protection therefore during packaging and shipment. The tubular means is preferably constructed from Pyrex or some other suitable relatively inexpensive material as compared to quartz tubing, the cost of which is appreciably higher than Pyrex. By utilizing a less expensive tubular means and providing means for reenforcing the same, the overall costs with respect to manufacturing the device on a production basis are materially reduced.

A significant object of the invention is to provide a supporting means for the purpose above described, which may be extended beyond the entrance of the tubular means whereby to pilot or facilitate flow of the liquid into the entrance.

Another object of the invention is to provide a device in which the wall structure preferably comprises a pair of moulded or formed half sections, each of which includes a relatively large portion provided with a recess and an extended or channel portion, whereby when the sections are correctly assembled the recesses will form the chamber, above referred to, and the channel portions will form a tubular formation which in certain of the devices hereinafter described, receives an inner extremity of a tubular means.

A further object of the invention is to provide a device which preferably includes an outer housing or casing which substantially surrounds the tubular formation formed by the channel portions of the half sections, the tubular means and the supporting means whereby to substantially maintain the components assembled. Cement may also be disposed in the housing whereby to assist in securing one or more of the components together.

A particularly significant objective is to provide a device in which the casing or housing thereof also serves as a grip or handle for attachment to a lance.

An important object is to provide a device or structure whereby one or more samples of predetermined size, weight and/or shape may be readily obtained.

Also, an object is to provide a device in which the half sections are preferably designed and constructed to accommodate appendage means whereby to facilitate identifying a sample or samples of metal obtained, including an improved method of attaching the appendage means to one or more samples.

A particular objective is to provide a modified device whereby samples of different shapes may be obtained, one of which, for example, may include a relatively large portion or head and one or more of which may be in the form of pin portions joined to the head, and the means utilized for obtaining one or more pin portions may also serve as a means for venting a chamber in which the head is formed as generally referred to above.

A specific object of the invention is to provide a modified device of the character described in the preceeding paragraph in which the means employed to obtain the sample which includes a head comprises the pair of half sections and the means for obtaining one or more pin samples comprises an outlet tube or tubes which are held between the sections and communicate with the chamber, the sections and outlet tubes are preferably imbedded in cement, and a housing or casing surrounds the sections and cement. This modified device also preferably includes a pair of telescoping inlet tubular means or tubes which are operatively associated with one another and the chamber whereby one of the tubular means extends beyond the other to support the latter and promote entry of a fluid into the one, and provide what may be termed a counter-recess or pocket for accommodating a deoxidizing element. The device may also include a plug confined within one end of the housing and filter means located between the plug and the outer ends of the outlet tubes.

A specific object is to provide a lance or wand with means, such as a connector which is so designed and constructed that any one of the devices disclosed herein may be readily detachably connected to the lance in any one of a number of infinite operative positions whereby to facilitate its use in obtaining a sample of liquid from a stream thereof. An important object is to provide an improved method or methods for obtaining one or more different samples of molten metal.

Another specific object of the invention is to provide a device having tubular means provided with an enlarged funnel or cup-shaped end to facilitate entry of metal into the tubular means.

A further object is to provide different forms of means for supporting the tubular means which initially receives the molten metal or fluid.

An important object is to provide a modified structure comprising a pair of different devices which are assembled in a side-by-side relationship substantially within an outer casing or housing and by suitable holding means so that samples of different shapes may be substantially simultaneously obtained.

A particularly significant object is to provide each of the devices of the modified structure described in the preceding paragraph with a pair of inlets or tubular means, and a support which is common to and supports the outer extremities of both tubular means.

Additional objects and advantages of the invention or inventions is to provide devices or structures which are reliable, efficient and comprised of a minimum number of components or parts which can be economically manufactured and assembled on a production basis, all of which is disclosed in the drawings annexed hereto and constitute portions of the subject application.

Referring to the drawings:

FIG. 20 is a side elevational view of a modified structure comprising a pair of devices whereby samples of different shapes may be obtained;

FIG. 21 is an end view of the structure depicted in FIG. 20;

FIG. 22 is a vertical section taken substantially on line 22—22 of FIG. 21;

FIG. 23 is a section taken substantially on line 23—23 of FIG. 20;

FIG. 24 is a section taken substantially on line 24—24 of FIG. 20;

FIG. 25 is a pictorial view of the samples obtained by using the composite structure shown in FIG. 20;

FIG. 26 is an end view of one of devices shown in FIG. 20, including an attached sample obtained from the other device;

FIGS. 27, 28, and 29 disclose different forms of means for supporting one or more tubular means;

FIG. 30 is a sectional view of a modified form of a device having a first or primary chamber and a pair of additional chambers;

FIG. 31 is a face view of a sample obtained by utilizing the device of FIG. 30;

FIG. 32 is a view similar to FIG. 30 showing three additional or secondary chambers connected to a primary chamber;

FIG. 33 is a face view of a sample obtained by using the device of FIG. 32;

FIG. 34 is an end view of the sections of FIG. 32 assembled;

FIG. 35 is an internal view of a portion of one of a pair of mating sections for use in a modified device;

FIG. 36 is an end view of a pair of sections of FIG. 35 assembled; and

FIG. 37 is a perspective view of a portion of a sample obtained by utilizing the assembly of FIG. 36.

Figure 1:
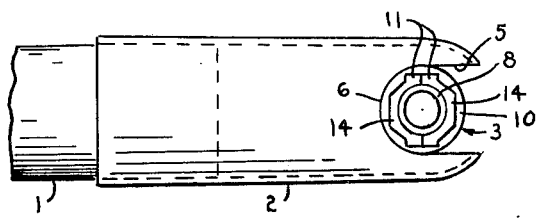
FIG. 1 is a partial view of a lance, staff or wand detachably supporting the device shown in FIGS. 3 and 4.
Figure 3A:
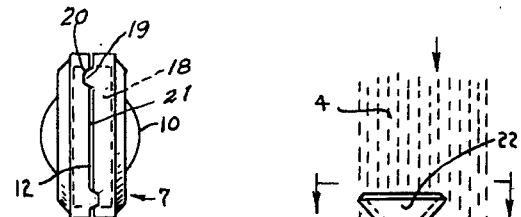
FIG. 3A is a partial end view of the device shown in FIG. 3.
Figure 3:
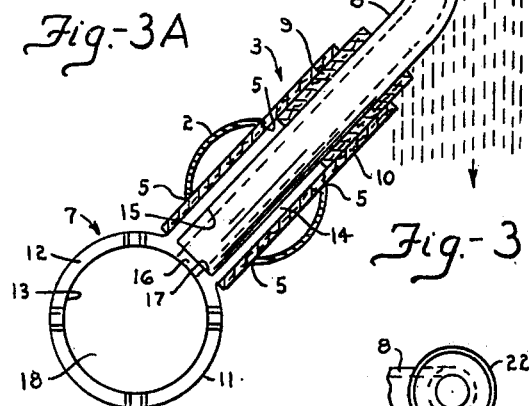
FIG. 3 is a view showing a device held in an inclined position by the lance for receiving a sample of molten metal from a stream thereof.
Figure 4:
FIG. 4 is a top view of a tubular means of the device shown in FIG. 3, provided with a funnel or cup-shaped end whereby to facilitate entry of metal into the device.
Figure 5:
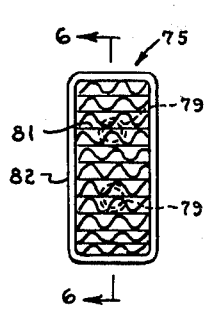
FIG. 5 is an end view of a modified device for obtaining one or more samples of different shapes.
Figure 6:
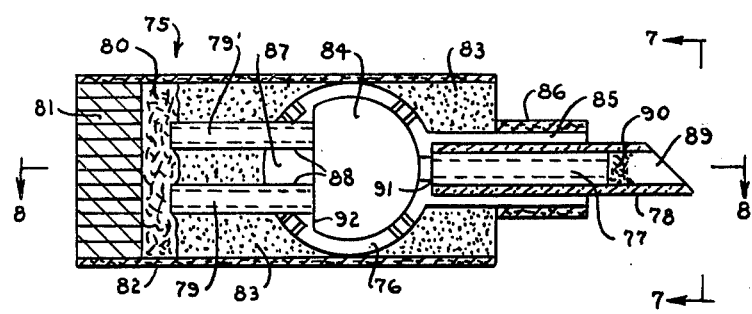
FIG. 6 is a transverse vertical section taken substantially on line 6—6 of FIG. 5.
Figure 8:
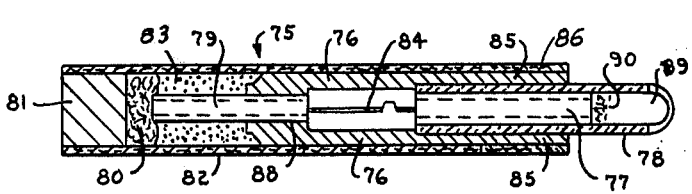
FIG. 8 is a horizontal section taken substantially on line 8—8 of FIG. 6.
Figure 7:
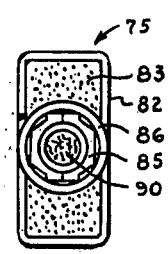
FIG. 7 is an end view of the device looking in the direction of the arrows 7—7 of FIG. 6.

Referring first to the structure exemplified in FIGS. 1, 3 and 4, there is shown a lance 1 provided with means, such as a connector 2, for detachably carrying a device generally designated 3, for use in obtaining a sample of liquid, such as molten metal from a stream 4 thereof as diagrammatically shown in FIG. 3. The lance 1 may be constructed of any material suitable for the purpose such as a length of pipe, sufficient to permit an operator to safely readily manipulate a device into and from a mass or stream of molten metal. The connector 2 may be designed and constructed in various ways but as depicted, preferably comprises a generally tapered hollow metal member which has an inner extremity fixedly telescopically attached to an end of the lance and an outer free extremity provided with a bifurcation for snugly accommodating the device 3 in a position substantially transverse to the longitudinal axis of the lance. The bifurcation actually provides two pair of notches, each notch being defined by a pair longitudinal marginal edges 5 and a merging inner curved edge 6. The furcations of the bifurcation preferably have sufficient flexible characteristics that the longitudinal edges 5 of the notches will preferably intimately engage, bite or frictionally grip the device at a location intermediate its length and hold it in any one of an infinite number of rotative positions about its own longitudinal axis and/or relative to the longitudinal axis of the lance or connector. More specifically in this respect, the device may be manually adjusted with respect to the connector, as shown, or it may be adjusted and automatically held in any one of an infinite number of oblique angular positions, the purpose of which is to offer an operator a multitude of options of standing in offside position whereby the device is always clearly visible whereby to facilitate safe and correct manipulation of the device with respect to a stream of molten metal for obtaining an uncontaminated sample thereof.

The device 3, as best shown in FIG. 3, preferably comprises a receiving means generally designated 7, tubular means 8, an inner sleeve 9, preferably made of pasteboard, and an outer cylindrical housing or casing 10 preferably of the same material. The receiving means may be designed and constructed in various ways but, as shown, preferably comprises a pair of half sections 11, each of which has an enlarged circular head portion 12 provided with a round recess 13 and an elongated channel or extended portion 14 having a semi-cylindrical groove 15 therein, and an intervening notch 16 forming an adjacent abutment 17 at the inner end of the groove 15. When the half sections are correctly assembled, the recesses 13 form a chamber or cavity 18 for receiving the metal sample and the channel portions 14 form what may be referred to as a tubular formation or which receives the tubular means or inlet tube 8. The edges or rims of the head portions 12 are preferably respectively provided with circumferentially spaced mating projections 19 and notches 20 whereby to assist in positioning the half sections and provide vents 21 in a manner substantially corresponding to those disclosed in my Patent above referred to. Obviously, the head, recess and other components may be other than circular or round.

The tubular means 8 is of appreciable length and preferably constructed of Pyrex or equivalent relatively inexpensive material as compared to quartz in order to withstand the high temperatures of molten metal. As shown the inner extremity of the tubular means is received in the tubular formation or grooves 15 in the channel portions 14 and engages the abutments 17 to limit its inward movement. It should be noted that the tubular means has an outside diameter which substantially corresponds to the internal diameter of the cylindrical opening formed by the grooves in the tubular formation so that the tubular means is preferably firmly frictionally held in place by the channel portions 14 through the agency of the outer casing 10 and that the internal diameter of the tubular means is slightly less or equal to that of an opening formed by the notches 16 so that the metal may flow freely into the chamber 18. The tubular means 8 has an outer extremity which extends beyond the tubular formation and is curved and provided with a cup or funnel-shaped end 22 whereby to pilot or facilitate entry of molten metal into the tubular means from the stream 4.

Attention is directed to the important fact that the inner sleeve 9 surrounds the outer extremity of the tubular means 8 and is snugly or frictionally held in the outer casing 10 whereby to assist in stabilizing, reenforcing or supporting the outer extremity of the tubular means in order to prevent breakage or damage thereto when it is introduced into a stream of metal. It should be noted that a portion of the sleeve 9 extends beyond an end of the casing whereby to impart added support for the tubular means. Otherwise expressed, the sleeve 9 constitutes a support for the tubular means for the purpose of alleviating breakage, due to the initial shock imparted to the tubular means upon its introduction into a stream of metal. This shock is the result of factors, such as the tremendous downward thrust, weight and heat of the molten metal.

Figure 2:
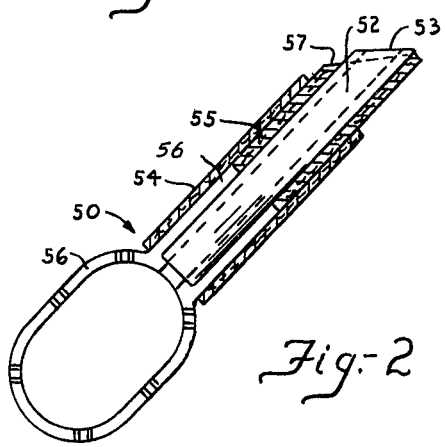
FIG. 2 is a longitudinal sectional view of a modified device.
Figure 9:
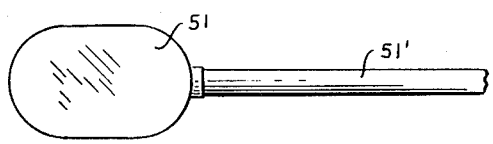
FIGS. 9 and 10 are face and side views of a sample obtained by utilizing the device depicted in FIG. 2.
Figure 10:
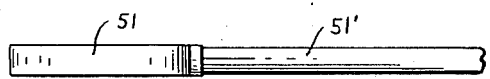

FIG. 2 depicts a modified device generally designated 50 similar to the device 3 but differs therefrom to the extent that it has an oblong chamber or cavity for obtaining as depicted in FIGS. 9 and 10 a sample having a flat head 51 of oblong shape and a stem or portion 51' as compared to a flat round head and stem obtained by the device 3. The device 50 also includes a tubular means 52 having an outer extremity provided with a beveled entrance end 53 whereby to facilitate entry of metal, an outer cylindrical casing 54 and an inner sleeve 55 having an inner extremity which engages the ends of a pair of half sections 56 (not shown) and an outer extremity which extends beyond an end of the casing 54 or adjacent to the beveled end 53 of the tubular means whereby to lend support to the outer extremity of the tubular means 52. It should be noted that an end of the sleeve 55 is preferably beveled as indicated at 57 which bevel is preferably greater than the bevel 53 in order to locate the entrance of the tubular means a predetermined distance in advance of the bevel 57 so that the metal with flow directly into the entrance of the tubular means 52. The device 50 offers a support for the tubular means through substantially its full length as compared to the device 3 depicted in FIG. 3. It is to be understood that if desired, the outer housings or casings 10 and 14 of the devices 3 and 50 may have other cross-dimensional shapes, such as square or rectangular and that cement may be utilized to hold one or more of the components assembled.

Figure 11:
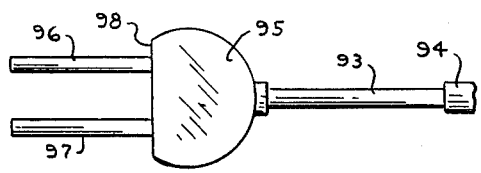
FIGS. 11 and 12 are face and side views of a sample or samples obtained by employing the device shown in FIG. 6.
Figure 12:
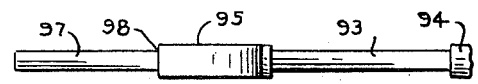

FIGS. 5 through 8 depict a modified device generally designated 75 whereby a sample or joined samples or portions as depicted in FIGS. 11 and 12 may be obtained. More particularly, the device 75 preferably comprises a pair of half sections 76 similar to the half sections of the device 3, an inner inlet tube or tubular means 77, an outer inlet tube or tubular means 78 surrounding the inner tube 77, a pair of corresponding parallel outlet tubes or tubular means 79 and 79' having the same internal diameters, filter means 80, plug means 81, an outer rectangular casing 82 and cement 83 in the casing 82 which substantially surrounds the major portions of the half sections 76 and the outlet tubular means 79 and 79' for maintaining the half sections assembled to form a chamber 84 and all of the tubes or tubular means assembled with the half sections. Obviously, internal cross-dimensions and the lengths of the tubular means 79 and 79' may be different. The half sections include channel or extended portions 85 which form a tubular formation of which a portion thereof extends outwardly from the cement and beyond one end of the casing 82. This formation is surrounded by a short sleeve 86 which assists in holding the channel portions 85 together, including the tubes or tubular means 77 and 78 in a cylindrical opening formed by mating grooves in the channel portions.

The half sections 76 are preferably respectively provided with relatively thick corresponding generally transversely disposed chordal portions 87 (one shown) having mating semi-cylindrical grooves therein. When the sections are assembled these grooves form cylindrical openings which respectively receive inner extremities of the outlet tubular means 79 and 79' so the latter will communicate with the chamber 84. More specifically, the cross-dimensions of the openings formed by the grooves 88 and the tubular means 79 and 79' are preferably such that when the sections are correctly assembled these tubular means are frictionally held therebetween.

The outer ends of the tubular means 79 and 79' preferably extend beyond the cement 83 for disposition in or against the filter means 80. This filter means and the plug means 81 maybe constructed of any material suitable for the purpose. More specifically, the filter means may be steel or fiber glass wool whereby to permit venting of air through the tubular means 79 and 79' into the filter means as the metal flows into the tubular means from the chamber 84, while substantially preventing escape of the metal from the tubular means. The plug means 81 is preferably a laminated unit comprising bonded layers of corrugated pasteboard material extending in planes parallel to the longitudinal axis of the device as shown. It is to be understood that although the outer tubes 79 and 79' are shown in a parallel relationship to the longitudinal axis of the device they may be disposed at oblique or different angles with reference to such axis, or a single tube in lieu of the pair may be located in axially spaced relation to the inlet tubes 77 and 78.

Attention is directed to the important fact that the inlet tubular means or tubes 77 and 78 are preferably constructed of material, such as Pyrex or equivalent relatively inexpensive material as compared to quartz and that they have different lengths and internal diameter. The outer larger and longer tube 78 is bevelled and extends beyond the inner tube 77 to provide what may be termed an entrance recess or pocket 89 within which is contained a conditioning means such as a deoxidizing element 90. The tube 78 serves to support the inner tube 77 and the recess 89 has a cross-dimension greater than the inside diameter of the inner tube whereby to pilot or facilitate entry of molten metal into the inner tube. In other words, the outer tube 78 serves the triple purpose of supporting the inner tube, piloting or guiding the metal into the chamber via the tube 77, and as a receptacle for a deoxidizing element. It should be noted that the half sections are also preferably provided with abutment means 91 (one shown) which serve to limit inward movement of the tubes 77 and 78 during their assembly in the portions 85. It should be manifest that since the channel portions 85 have a length greater than one half the length of the tube 78 it may be stated that the outer extremity of the tube 78 is supported by the channel portions 85.

Attention is also directed to the fact that the device 75 is preferably generally rectangular in cross-section and it is obvious that a connector such as 2, above referred to, may be notched to the correct size, if required, to detachably receive this device. Obviously, this device may have a cross-section other than square or rectangular. The connector is unique since it will accommodate casings which are round, oval, square or rectangular in cross-section.

As alluded to above, FIGS. 11 and 12 depict face and side views of a sample, samples or portions which can be obtained by employing the device 75. More specifically, numeral 93 designates a stem or pin portion formed in the inlet tube 77, 94 a portion formed in the tube 78, 95 an intermediate relatively large portion or head formed in the chamber 84, and pin portions 96 and 97 formed in the outlet tubes 79' and 79. It is to be understood that the designs or shapes shown may be considered to represent a single composite sample or several samples or portions. The pin portions 93, 96 and 97 are preferably disposed with respect to the intermediate or head portion 95 so that any one or all of the portions may be separated and utilized for analysis. It should be noted that the portion 95 has a uniform thickness which is greater than the cross-dimensions of the other portions and is substantially round except for its chordal marginal edge 98. It is to be understood that the cross-dimension and length of the various portions may be modified by changing the dimensions of the chamber and tubular means of the device.

Figure 13:
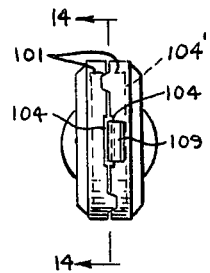
FIG. 13 is an end view of a modified device illustrated in FIG. 14.
Figures 14, 15:
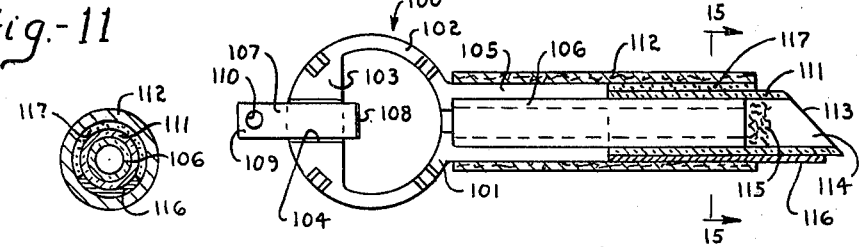
FIG. 14 is a vertical section taken substantially on line 14—14 of FIG. 13.
FIG. 15 is a transverse section taken substantially on line 15—15 of FIG. 14.

FIGS. 13, 14 and 15 illustrate a modified device generally designated 100 comprising, among other things, a pair of half sections 101 having head portion 102 forming a chamber and thick chordal portion 103 provided with axially extending rectangular recesses 104, including channel or extended portions 105 having grooves therein whereby to form a tubular formation for receiving an inner or center tubular means or tube 106 of Pyrex or equivalent material. The recesses 104 define an opening through which an appendage 107 of metal extends so that an inner offset end 108 is located in the chamber for imbedment in a sample and an outer offset end 109 provided with an aperture 110 to facilitate attachment of identification means to the appendage.

Attention is directed to the face that the device 100 may be utilized without the appendage 107, in which event, the recesses 104 will define a secondary chamber so dimensional that when filled with molten metal, a sample of approximtely 1 gram is formed to satisfy the requirements of certain devices on the market to determine carbon or other element percentages using 1 gram (± 40%) of weight. The outer end of the secondary chamber may be closed by means, such as a piece of tape or mastic 104 as shown by the dotted lines in FIG. 13.

The tube 106 is relatively long and has an outer extremity which is surrounded by a larger but shorter outer tube on tubular means 111 of Pyrex or equivalent material having an end which extends outwardly from an outer cylindrical housing or casing 112 of pasteboard or equivalent material and is provided with a bevelled entrance 113. The inner end of the tube 111 preferably abuts outer ends of the channel portions 105 of the half sections and its outer extremity serves to support the outer extremity of the inner tube 106. The outer tube 111 extends a short distance beyond the tube 106 to provide a recess or pocket 114 which serves to pilot metal into the tube 106 and contain a deoxidizing element 115.

Attention is directed to the fact that the outer tube 111 is stabilized or supported by a support as supporting means 116, arcuate in cross-section, which has an inner end interposed between the casing 112 and the tube 111 so that an outer end of the support will extend outwardly beyond an end of the casing for supporting the entrance end of the tube 111. It should be manifest that the tube 111 and support 116 separately and jointly support the tube 106. The casing 112 serves to hold the half sections assembled and heat resistant cement or mastic 117 is preferably placed between the casing and an upper portion of the tube 111 whereby to assist in holding the components assembled. The cement 117 or mastic and casing 112 also assist in supporting the tubes 111 and 113 and the support 116. It is to be understood that in some instances, the portions 105 of the half sections and the tube 106 may be defined as constituting tubular means or structure, in which event, the tube 111 and/or the support 116 may constitute means for supporting the outer extremity of the tube 106, or the tubular means may include the tubes 106 and 111 which are supported by the support 116. Also, the tubular means may include the portions 105, tubes 106 and 111, in which event, the support 116 supports the outer extremity of an entity comprising these components.

The sample or portions thereof obtained by the device 100 will include a portion similar the portion 95 described above, in which the appendage 107 is anchored thereto, and a cylindrical extension or stem portion and a portion which are similar to the portions 93 and 94 described above.

Figure 16:
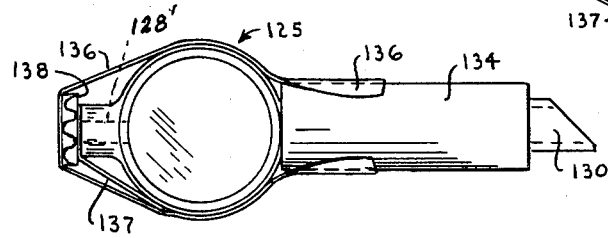
FIG. 16 is a side view of a modified device.
Figure 17:
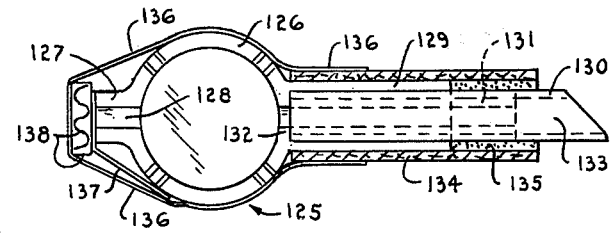
FIG. 17 is a longitudinal section taken on FIG. 16.
Figure 18:
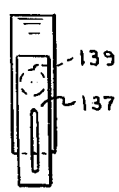
FIGS. 18 and 19 are end and side views of a sample or samples obtained by using the device shown in FIGS. 16 and 17.
Figure 19:
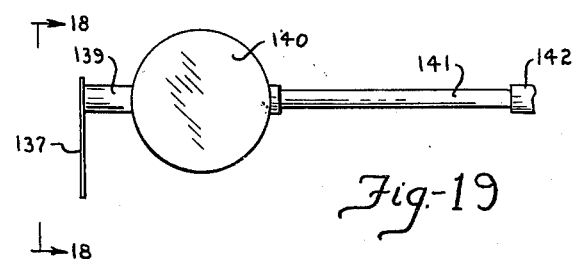

A modified device generally designated 125 is depicted in FIGS. 16 and 17 for obtaining a sample or sample portions as shown in FIG. 18 and 19. This device comprises a pair of recessed half sections 126 (one shown) which substantially corresponds to those designated 101 of the device 100, except that the head portions of the sections are thickened to provide outwardly extending portions 127 having semi-cylindrical mating grooves 128 (one shown) therein whereby to form what may be termed a secondary receiving means, chamber, or cavity 128′ of a predetermined axial length and cross-dimension for receiving metal from a primary chamber formed by the recessed head portions of the sections. The half sections 126 have channels or extended portions 129 forming a tubular formation which receives inner extremities of a pair of tubular means or tubes 130 and 131 of Pyrex or equivalent material. The half sections are formed to provide abutment means 132 which is common to and engaged by inner ends of the tubes 130 and 131 to limit their inner movement. It will be noted that the diameter of the tube 131 is less than that of the tube 130 for telescoping movement therein and is also shorter than tube 130 so an outer extremity of the latter extends outwardly beyond the inner tube to provide a recess of pocket 133 for receiving a deoxidizing element, if so desired. The half sections are preferably held assembled by an outer cylindrical housing or casing 134 of pasteboard or equivalent material which surrounds the portions 129 of the half sections and extends therebeyond to form a cylindrical recess between the outer tube 130 and the extended portion of the casing which is preferably filled with heat resistant cement 135 whereby to anchor the tube 130 in place and firmly support its outer extremity a portion of which extends a short distance beyond the casing and is provided with a bevelled entrance to facilitate entry of a liquid.

The half sections 126 of the device 125 are also preferably held assembled, at least to some extent, by suitable means such as tape 136 which is secured to the sections as shown.

Attention is directed to the fact that the device 125 is provided with an appendage 137 having an extremity disposed across the secondary chamber 128′ and with a slotted free extremity. This appendage is held in place by a filter means 138 through the agency of the tape. When a sample is being obtained it will flow successively into the tubes 130 and 131, successively into the primary and secondary chambers in so doing some air will be vented out through the secondary chamber and through and/or along the sides of the filter means 138 just before the molten metal engages the appendage but when the metal does engage the appendage it causes a small localized portion thereof to melt sufficiently to automatically weld itself to a pin portion 139 of a sample obtained as depicted in FIGS. 18 and 19. This mode of automatically attaching an appendage to a sample to faciliate its identification is considered to constitute a meritorious advance in the art. The sample also includes a relatively large thick flat round portion 140 and a stem, extension or cylindrical pin portion 141 and a small cylindrical portion 142, having a diameter greater than that of the pin portion 141, which is formed at the entrance end of the device. Any one or all of these portions may be separated from one another and utilized for analysis. Obviously, half sections and and tubes may be designed and constructed to provide sample portions of different shapes and cross-dimensions.

Referring now to FIGS. 20 through 24 there is disclosed a composite structure comprising a pair of devices generally designated 150 and 151 which are secured together in a side-by-side relation whereby samples of different shapes as depicted in FIG. 25 may be substantially simultaneously obtained.

More specifically, the device 150 preferably comprises a pair of half sections 152 and 153 having enlarged or round portions provided with mating recesses which form a chamber 154 including channel or extended portions 155 provided with mating semi-cylindrical grooves which form a tubular formation for receiving a relatively short cylindrical tube or inner tubular means 156 and an inner extremity of an outer tube or tubular means 157. These tubes are preferably constructed of Pyrex or equivalent material and disposed in an end-to-end abuting relationship. It will be noted that cement or refractory material 158 substantially surrounds major portions of the tubular means 157 and that a portion of the latter extends outwardly from an end of an outer casing 159, preferably rectangular in cross-section and constructed of pasteboard. It should also be noted that the tubes 156 and 157 have the same outside diameter and that the inside diameter of the tube 156 is somewhat less than the inside diameter of the tube 157 so that a cylindrical or stem portion 160 is formed in the tube 156, a cylindrical portion 161 is formed in the tube 157, and a head portion 162 is formed in the chamber 154 as shown in FIG. 25. Attention is directed to the fact that the internal diameter and length of the tube 156 is predetermined so that for example the portion 160 formed therein has a predetermined weight to length ratio, such as, for example, 1 gram, when severed from the portions 161 and 162. Obviously, one or more tubes like 156 may be utilized to obtain one or more portions which are shorter, longer and of different cross-sectional dimensions.

The cement, mastic, or refractory 158 serves to firmly secure the tubes 156 and 157 in place and the casing 159 assists in holding the half sections assembled. The sections are preferably provided with abutment means 163 which limits inward movement of the tube 156.

The other device generally designated 151 of composite structure shown in FIGS. 20, 21, 22, 24 and 26 comprises an elongated tubular means or tube 164 of Pyrex or equivalent material having an inner extremity surrounded by a sleeve 165 preferably made of pasteboard or equivalent inexpensive material and an outer extremity which is surrounded by a larger but shorter Pyrex tubular means or tube 166, the latter of which has an extremity extending beyond the casing 159 the same distance as the tube 157 of the device 150 and is provided with a bevelled entrance. It should be noted that the inner end of the sleeve 165 is formed to provide an abutment 167 for limiting inward movement of the tube 164.

Attention is directed to the significant fact that an elongated support 168 has an inner extremity imbedded to the cement or refractory material 158 and an outer extremity which is common to and supports the outer extremities of the tubes 166 and 157. This support, as depicted in FIG. 21, is preferably provided with a pair of corresponding parallel channels 169 of arcuate cross-section which respectively receive the tubes 166 and 157 and an intervening channel 170 also of arcuate cross-section which is at least partially interposed between these tubes in order to assist in locating and stabilizing their positions. The inner extremity of the support 168 by its imbedment in the cement also serves to impart stability and durability to the structure. The cement also preferably substantially surrounds the sleeve 165.

The device 151 also preferably includes a filter means 171 comprising a unit of bonded laminations of pasteboard which allows air to escape therethrough from the tube 164 but not metal and a shroud or tape 172 is preferably attached to or at least partially wrapped about the outer extremities of the devices 150 and 151 whereby to assist in holding the filter means 171 in relation to the tube 164 and the devices assembled and protected. The tape may be constructed of any material suitable for the purpose and if a shroud is used it may be of aluminum foil, or fiber glass. Obviously, the filter means may be constructed from any material suitable for the purpose.

Attention is directed to the fact that a unique appendage of metal generally designated 173 may be employed to facilitate identification of the samples obtained from the two appendage 173 devices. More specifically, FIGS. 22 and 26 show that the appendage includes an end 174 which extends into the chamber 154 of the device 150 through an opening 175 provided therefor and an offset end 176 located between the outer end of the tube 164 and sleeve 165 and the filter means 171. The opening 175 is formed by mating recesses provided in the half sections. The appendage also has a bridge portion which is held between an inner side of the filter means and the half-section 153. It will be noted that the laminations of the filter means extend in planes in line with or parallel to the axis of the tube 164 and that the tape or shroud 172 assists in holding the appendage and filter means in place prior to submission to molten metal.

The device 151 enables one to obtain a cylindrical pin sample portion 177 having a predetermined diameter and length and a larger but shorter portion 178 obtained from the tubes 164 and 166. The offset 176 of the appendage 173 is preferably automatically bonded to the portion 177 by melting a localized area of the offset to affect a weld between the offset and portion 177 and the hot metal flowing into the tube 164 and the end 174 of the appendage is anchored or bonded to the molten metal which enters the chamber 154.

It is to be understood that supports having shapes different from the support 168 may be utilized. For example, a generally rectangular planar support 180 as shown in FIG. 27 may be employed, or one such as 181, which is rectangular and concave-convex in cross-section as depicted in FIG. 28 may be used to advantage. The supports 180 and 181 may be used to support the tubes 157 and 166 in lieu of the support 168 and all of these supports may be employed to support tubes having the same or different diameters as depicted and lengths and/or combinations of one within another. Also, if so desired, a supporting means generally designated 182 so shown in FIG. 29 may be employed. This supporting means is generally arch or U-shaped and constructed from wire to include a pair of legs 183 and a bridge 184 for use in supporting the tubular means 106 and 111, of FIG. 14, in lieu of the supporting means 116, in which event the legs 183 could be located between the tubular means 113 and the casing 112, with portions of the legs and/or bridge engaging the tubular means 113 for supporting the same. Obviously, the supporting means 182 could be of a greater width whereby to support the pair of tubular means shown in FIG. 22.

Summarizing the above in a general way it is to be understood that all of the devices described are capable of being readily detachably connected to a lance through the agency of a connector, such as 2; that the device 75 offers a setup whereby several sample portions of predetermined shapes may be readily obtained for analysis; that tubular means or structure of the same or different diameters and lengths may be utilized to obtain sample portions of predetermined shapes, sizes or weights; that one of the appendages shown is common to and joined with at least a pair of sample portions in a unique way to facilitate identification thereof; that various forms of supports for supporting one or more inlet tubes may be employed to advantage; that all of the devices are preferably adapted for attachment to a lance in a position substantially transverse thereto whereby to promote safety since an operator is offered many standing positions with respect to a stream of molten metal to better view the penetration of the entrance end of the device into the stream; that the devices are constructed and arranged for manufacture on a production basis; and that the outer casings of the devices may be considered to constitute handles, grips or components which are received in the connector.

Attention is directed to the fact that bevelled entrances of the tubular means of all of the devices are preferably disposed in a predetermined position with respect to the primary chambers or receiving means, so that when any device is being so used its chamber will generally be in a substantially vertical plane and this will allow the molten metal to flow initially downwardly as it enters the chamber.

FIG. 30 depicts a modified device and FIG. 31 a sample obtained therefrom. More particularly, numeral 200 generally designates the device which comprises wall structure, preferably in the form of a pair of mating or half sections, of which one 201 is shown in FIG. 30. Each section includes wall structure forming an enlargement or head 202 provided with a large recess 203 and a reduced or extended portion 204 provided with an outer groove 205, an inner groove 206 smaller than the inner groove and a tapered intermediate groove 207. When the sections or wall structure are correctly assembled as substantially depicted in the modified assembly of FIG. 34, the recesses 203 will form: a first or primary chamber which is generally oblong in shape (it may be of any other shape); the outer grooves 205 a tubular formation having an entrance; the inner grooves 206 a tubular passage having a diameter somewhat less than that of the entrance; and the tapered grooves 207 an intermediate tapered or mixing chamber which funnels the molten material or metal into the passage.

The extended portions 204, as noted above, form a tubular formation and a tubular means, preferably in the form of a Pyrex tube 208 or other suitable material has an inner extremity secured in the entrance formed by the other grooves 205 and an outer extremity provided with a bevelled entrance for initially receiving the molten material. A tubular spacer 209, preferably made of pasteboard, is secured about the tube 208 to impart stability thereto and a sleeve or casing 210, preferably of pasteboard, is secured about the extensions 204, spacer 209 and tube 208 whereby to assist in maintaining the components assembled. The spacer 209 and casing 210 are preferably square in cross-section.

A deoxidizing means preferably in the form of a conical coil 211 is partially held in the intermediate chamber and extends forwardly in the tube 208. The incoming molten material or metal melts the means 211 and mixes therewith in the intermediate chamber to condition the metal, preferably prior to its flow into the primary chamber through the passage formed by the inner grooves 206.

The sections have outer curved portions or rim portions 213 (one shown) which are relatively thick and preferably provided with a pair of corresponding tapered grooves 214 and 215 which extend generally radially outwardly or at angles with reference to or on opposite sides of the longitudinal axis of the device. The internal surfaces defining the pairs of grooves 214 and 215 form a pair of tapered smaller or secondary chambers like the outermost chambers shown in FIG. 34 which are communicatively connected to the primary chamber and receive the molten material therefrom whereby to obtain a sample S having a pair of projecting or extended sample portions 218 and 219 as depicted in FIGS. 31, including the additional portions 220, 221, 222, and 223 which are formed in the structure described above. The enlarged or head portions 202 of the sections 201 are preferably provided with locating means preferably in the form of mating notches and projections as shown in FIGS. 3A, 13, 26 and 36 whereby to assist or facilitate their assembly and afford relief or vents to promote the inflow of the molten material into the various chambers. It may be stated that the grooves 214 and 215 define a vent.

FIGS. 32 and 33 substantially respectively correspond to FIGS. 9 and 10 of my copending application Ser. No. 563,590 filed Mar. 31, 1975 and substantially respectively correspond to FIGS. 30 and 31 of the subject application, except that three tapered additional or secondary grooves 226, 227 and 228 are disclosed in FIG. 32 and three sample portions 229', 230' and 231', preferably of predetermined sizes or weights of 1 gram each, are shown in FIG. 33.

More particularly, in FIG. 32 there is depicted a device generally designated 300. This device, among other things, comprises wall structure, preferably comprising a pair of recessed mating sections 232 having head portions or enlargements and extended portions 234, and which when assembled form a first or primary chamber and a tubular formation. An outer portion of each of the sections is preferably relatively thick as indicated at 232' and provided with the grooves 226, 227 and 228, above referred to, which form three generally corresponding secondary chambers 229, 230 and 231, as shown in FIG. 34, which receive the molten material from the primary chamber and form the sample portions 229', 230' and 231'. Each of the grooves is preferably defined by base surface and side surfaces and these surfaces are disposed within the confines of the head portions of the sections.

The extended portions 234 of the sections 232 of the device 300 are also provided with grooves corresponding to those shown in FIG. 30. This device also includes a tube 235, sleeve 236, a casing 237 and deoxidizing means 258. Those grooves corresponding to the grooves 206 and 207 and the tube 235 corresponding to the tube form a sample S having sample portions 239, 240 and 241 of a sample S and of course the primary chamber forms a head portion 241'.

In FIG. 34, the sections 232 are shown assembled, with metal appendages 242, 243 and 244 havng intermediate portions which are respectively disposed at the secondary chambers 242, 243 and 244 and outer extremities. A means 245, preferably in the form of an adhesive metallic tape, serves to hold the appendages in place and substantially prevent the outflow of the molten material from the secondary chambers so that the extended sample portions 229', 230' and 231' are well shaped to predetermined sizes or weights desired. The means 245 is common to all of the appendages and may also serve to secure the head or enlarged portions of the sections together. The outer end extremities of the appendages are preferably of a sufficient length so that they will extend laterally from the means 245 in order that identification tags may be attached thereto. It should be noted that the intermediate portions of the appendages are so disposed in relation to the secondary chambers that the molten material flowing into these chambers will automatically bond itself to the appendages at locations substantially exteriorly of the chambers. In some instances the bond may be in the form of what may be termed a tack weld while in other instances some of the intermediate portions may be partially enveloped by the molten material, both instances of which are illustrated in FIG. 33. The extended sample portions are intended to be severed from the head portion 241' and if so desired, the portions 239, 240 and 241 may be severed from one another for analysis. It is to be noted that the secondary grooves 227 form a secondary chamber which is located on the longitudinal axis of the device and that the other grooves form secondary chambers disposed on opposite sides of this axis. It should be understood that the shapes of all of the chambers formed by the wall structure may be varied as desired. For example, the shape of the primary or first chamber may be generally round as shown in my copending application Ser. No. 563,590, or may be spheroidal or triangular and the secondary chambers may be formed by generally rectangular grooves, as distinguished from the generally semi-cylindrical ones shown.

It is also to be understood that all of the secondary chambers disclosed in the subject application may be defined as constituting continuations of the first or primary chamber and that the portion or portions 213 and 232 of FIGS. 30 and 32 above described and portions 403 hereinafter described in FIG. 35 may be defined as outer, end, curved, solid or thick. The portions 403 in FIG. 35 may also be defined as being chordal. Moreover, the sections 232 may be contructed as shown or if so desired, one section may be formed to substantially provide a primary chamber and secondary chambers and the other section may constitute what may be termed a cover therefor. Otherwise expressed, it is desirable that the sections mate with one another, irrespective of their shape.

The modified device or structure generally designated 400 is exemplified in FIGS. 35 and 36 and the sample generally designated 401 obtainable thereby as shown in FIG. 36 will now be described. This device includes wall structure in the form of a pair of sections 402 which when assembled provide a first or primary chamber and a tubular formation like that of FIGS. 30 and 32. This device may also include other components corresponding to those shown in FIGS. 30 and 32.

The sections 402 have enlargements or head portions which are preferably formed with relatively thick chordal or rim portions 403, each of which is provided with an inner groove 404, an outer groove 405 having a cross-dimension somewhat less than that of the inner groove, and an intermediate transversely disposed oval shaped recess 406. When the sections are correctly assembled, this arrangement of grooves and recesses define an inner passage, an outer passage and an intermediate secondary chamber so that when the device is utilized molten material will flow into the primary or first chamber and then successively into the inner passage, secondary chamber and outer passage to form the sample 401 having a head portion 407 and portion 408, 409 and 410 as shown in FIG. 37.

As illustrated in FIG. 36, a metal appendage 411 is preferably held in place over the outer passage by means 412, preferably in the form of an adhesive metallic tape for substantially preventing the outflow of material from the outer passage, or otherwise retain sufficient material in the passages and secondary chamber to obtain wall formed or shaped sample portions, and particularly the portion 409 which is of a predetermined size or weight, for example, 1 gram in weight for analysis. It should be noted that the portions 408 and 410 are preferably cylindrical in shape and that the oval portion 409 has planar surfaces, and that the portion 408 constitutes an intermediate restricted portion joining portions 407 and 409. The appendage 411 is affixed to the sample portion 410 in either of the instances described above with respect to FIG. 33. It is to be understood that the sections may be designed and constructed in various ways other than shown; that the inner and outer passages and secondary chamber may be shaped other than shown; and that the portions 408 and 410 may have cross-sectional dimensions different from those shown. Furthermore, the passages actually constitute an elongated passage means or duct which is enlarged intermediate its extremities to form a secondary chamber or cavity. Also, it is to be understood that the secondary chambers receive molten material from the first chamber in a generally flow through direction from the entrance leading to this first chamber. Although the portions 407 and 409 are primarily intended for separation for analysis, it is to be understood that the portions 408 and 410 may also be utilized for analysis.

Attention is directed to the fact that the inner and outer grooves and recesses forming the passage and secondary chamber are all disposed within the confines of the sections and particularly within the confines of the heads or enlarged portions of the sections. Also, it is to be understood that the passages may also be considered to constitute additional or secondary chambers. Attention is also directed to the fact that the cross sectional dimensions of a spacer and casing for use with all of the devices 200, 300 and 400 are preferably noncircular or multi-sided in cross-section. Moreover, the passages and secondary chamber as formed by the grooves and recesses as disclosed in FIGS. 35 and 36 is considered to constitute a meritorious advance in the art of sampling molten material, such as molten metal.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. A device for obtaining a sample of flowable material from a supply thereof, said device comprising wall structure forming a first chamber, tubular means communicating with and extending from said chamber for receiving such material for flow into said chamber for solidification therein, said wall structure also forming a second chamber disposed substantially opposite said tubular means for receiving such material from said first chamber for solidification therein for analysis, and an appendage having a portion disposed in said second chamber for attachment to such material and a portion disposed exteriorly thereof.

2. Structure constituting a subassembly of a device for obtaining a sample of molten metal, said subassembly comprising a pair of half sections, each of said sections having a head provided with a recess and an extended portion provided with a groove, said head of each section also having a relatively thick chordal portion provided with a longitudinal groove spaced from the groove in the extended portion, the arrangement being such that when said sections are correctly assembled, said recesses and the grooves in the extended portions will respectively form a primary chamber and an opening, and said grooves in said chordal portions will form a secondary chamber for receiving metal from said primary chamber whereby to obtain a sample substantially entirely within the confines of said chambers and head to form a large portion and a smaller portion of a predetermined size extending from said large portion.

3. A subassembly for use as a component of a device for obtaining a sample of molten material from a supply thereof, said subassembly comprising wall structure forming an enlargement provided with internal surfaces forming a primary chamber and a reduced tubular formation having an entrance, and said enlargement substantially axially opposite said entrance being provided with internal surfaces forming a secondary chamber whereby molten material entering said entrance will flow in a direction generally toward said secondary chamber via said primary chamber for eventual solidification against the internal surfaces of said chambers to provide a sample having a large portion and a smaller portion of a predetermined size within the confines of said enlargement.

4. The structure defined in claim 3, including an appendage having at least a portion thereof disposed in said secondary chamber.

5. A structure for use as a means of a device for obtaining a sample of molten material from a supply thereof, said structure comprising walls forming an enlargement provided with internal surfaces forming a primary chamber having an entrance, said enlargement also being provided with internal surfaces forming a secondary chamber located generally axially opposite said entrance whereby the molten material entering said entrance will flow substantially freely and successively into said primary and secondary chambers for eventual solidification against the internal surfaces thereof whereby to form a sample substantially within the confines of said chambers which has a large portion and a smaller portion of a predetermined size extending from said large portion, and means for substantially preventing the outflow of molten material from said secondary chamber.

6. The structure defined in claim 5, in which said wall structure comprises a pair of molded sections which are respectively provided with the internal surfaces whereby to define the primary and secondary chambers when the sections are assembled, and said sections are respectively provided with channel portions which in combination define the tubular formation.

7. The structure defined in claim 5, including tubular means secured in relation to said tubular formation for communication with said primary chamber.

8. A structure for use as a means of a device for obtaining a sample of molten material from a supply thereof, said structure comprising walls forming an enlargement provided with internal surfaces forming a plurality of communicatively connected chambers and an entrance communicatively connected to all chambers for receiving material for flow into said chambers and against said surfaces for solidification therein, and means engaging said enlargement for substantially preventing the outflow of the molten material from said chambers whereby the material when solidified will form a sample disposed substantially entirely within the confines of said chambers.

9. The structure defined in claim 8, in which one of said chambers constitutes a vent to promote the flow of the material into the chamber.

10. A subassembly of a device for obtaining a sample of molten material from a supply thereof, said subassembly being provided with internal surfaces forming a first chamber provided with an entrance and thickened rim portion disposed generally axially opposite said entrance, and said rim portion being provided with internal surfaces forming a plurality of additional divergently disposed chambers whereby molten material entering said entrance will flow successively into said first chamber and said additional chambers for eventual solidification against the internal surfaces of said chambers to provide a sample having a large portion in said first chamber and smaller portions of predetermined sizes within the confines of said rim portion.

11. A subassembly of a device for obtaining a sample of molten material from a supply thereof, said subassembly being provided with internal surfaces forming a first chamber provided with an entrance and rim structure having a portion thereof disposed generally axially opposite said entrance, and said rim portion being provided with internal surfaces forming elongated passage means which is enlarged intermediate its length to form (a) transverse an oblong second chamber disposed transverse to said passage means whereby molten material entering said entrance will flow into said second chamber via said first chamber for eventual solidification against the internal surfaces of said chambers to provide a sample having a large portion formed in said first chamber and a smaller oblong portion of a predetermined size in said second chamber substantially within the confines of said rim structure.

12. The subassembly defined in claim 11, in which said passage means has an outlet, including means disposed over said outlet for substantially preventing the outflow of molten material therefrom.

13. The subassembly defined in claim 11, in which said passage means has an outlet, including an appendage disposed at said outlet, and means for holding said appendage in place and substantially retaining molten material in said second chamber.

14. A device for obtaining a sample of molten material from a supply thereof, said device comprising wall structure forming a first chamber, tubular means for receiving such material for flow into said first chamber and said wall structure generally opposite said tubular means having a relatively solid area provided with a plurality of closely related divergent second chambers for directly receiving material from said first chamber, this arrangement being such that when the material eventually solidifies a sample having a large portion will be formed in said first chamber and smaller portions will be formed in said second chambers and within the confines of said solid area.

15. The device defined in claim 14, including means common to said second chambers for substantially retaining the molten materials therein.

16. The device defined in claim 15, including a plurality of appendages which are respectively secured for attachment to said smaller sample portions at locations substantially exteriorly of said second chambers.

17. A subassembly for use in a device for obtaining a sample of molten material from a supply thereof, said subassembly comprising a chamber having an entrance and a thickened rim portion provided with at least a pair of cavities disposed generally away from said entrance for receiving molten material for flow into said cavities from said chamber, and external means for substantially preventing the outflow of material from said cavities whereby when the material solidifies a portion will be formed in said chamber and smaller portions will be formed in said cavities and within the confines of said rim portion.

18. A device for obtaining a sample of molten material from a supply thereof, said device comprising a casing, wall structure disposed in said casing and forming a primary chamber provided with an entrance for receiving the material and a secondary chamber for receiving the material from said primary chamber, and fibrous means secured in said casing serving to substantially prevent the outflow of the molten material from said secondary chamber.

19. A structure for use as a means of a device for obtaining a sample of molten material from a supply thereof, said structure comprising walls forming: an enlargement provided with internal surfaces forming a primary chamber; a plurality of additional chambers communicatively connected to said primary chamber and an entrance through which the material may flow into said chambers for solidification to form a sample therein, and means engaging said enlargement for substantially preventing the outflow of the molten material from at least two of said additional chambers whereby said sample is disposed substantially within the confines of said chambers prior to removal therefrom.

20. The structure defined in claim 19, in which said additional chambers are smaller than the primary chamber and extend outwardly therefrom.

21. The structure defined in claim 19, in which said additional chambers extend generally radially outward from the primary chamber and are smaller and tapered.

22. The structure defined in claim 19, including a casing within which said structure is disposed, and said preventing means is of a fibrous character and held in place by said casing.

23. The structure defined in claim 19, including tubular structure communicatively connected to said entrance for initially receiving the molten material for flow thereto.

24. A sample of metal formed from a supply of molten metal, said sample comprising an intermediate large portion, a stem portion extending therefrom, and a plurality of additional divergent symetrical portions which extend outwardly from said large portion in directions opposite to that of said stem portion.

25. The sample defined in claim 24, in which said large portion is elongated.

26. The sample defined in claim 24, in which said large portion is provided with a surface disposed transverse to said stem and said additional portions extend from said surface.

* * * * *